United States Patent
Morschhäuser et al.

(10) Patent No.: US 7,186,774 B2
(45) Date of Patent: Mar. 6, 2007

(54) SILICONE-MODIFIED COMB POLYMERS BASED ON ACRYLOYLDIMETHYLTAURINE ACID (2-ACRYLAMIDO-2-METHYL-1-PROPANESULFONIC ACID)

(75) Inventors: Roman Morschhäuser, Mainz (DE); Jan Glauder, Frankfurt (DE); Matthias Löffler, Niedernhausen (DE); Susan Rudloff, Kelkheim (DE); Sonja Klein, Hattersheim (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 430 days.

(21) Appl. No.: 10/433,118

(22) PCT Filed: Nov. 28, 2001

(86) PCT No.: PCT/EP01/13858

§ 371 (c)(1),
(2), (4) Date: Nov. 17, 2003

(87) PCT Pub. No.: WO02/44225

PCT Pub. Date: Jun. 6, 2002

(65) Prior Publication Data

US 2005/0232887 A1    Oct. 20, 2005

(30) Foreign Application Priority Data

Dec. 1, 2000   (DE) ................ 100 59 831

(51) Int. Cl.
   *C08F 228/02*   (2006.01)
(52) U.S. Cl. ............... 524/555; 524/458; 524/461; 526/264; 526/265; 526/279; 526/288; 526/307.7; 526/318.4; 526/323.2
(58) Field of Classification Search ........... 526/264, 526/265, 279, 288, 307.7, 318.4, 323.2; 524/458, 524/461
See application file for complete search history.

(56) References Cited

U.S. PATENT DOCUMENTS

| | | | |
|---|---|---|---|
| 4,606,933 A | 8/1986 | Griswold et al. | 427/54.1 |
| 5,368,850 A | 11/1994 | Cauwet et al. | 424/70 |
| 5,879,718 A | 3/1999 | Sebillote-Arnaud | 424/705 |
| 6,120,780 A | 9/2000 | Dupuis et al. | 424/401 |
| 6,310,116 B1 * | 10/2001 | Yasuda et al. | 523/106 |
| 6,403,074 B1 | 6/2002 | Blankenburg et al. | 424/70.12 |
| 6,419,912 B1 | 7/2002 | Lezer et al. | 424/78.03 |
| 6,468,549 B1 | 10/2002 | Dupuis et al. | 424/401 |
| 6,524,564 B1 | 2/2003 | Kim et al. | 424/70.12 |

FOREIGN PATENT DOCUMENTS

| | | |
|---|---|---|
| DE | 199 07 587 | 8/2000 |
| DE | 199 07 715 | 8/2000 |
| DE | 199 51 877 | 5/2001 |
| EP | 0 356 241 | 2/1990 |
| EP | 0 509 853 | 9/1992 |
| EP | 0 815 844 | 1/1998 |
| EP | 0 815 845 | 1/1998 |
| EP | 0 816 403 | 1/1998 |
| EP | 1 083 184 | 3/2001 |
| FR | 2 791 558 | 10/2000 |
| WO | WO 98/00094 | 1/1998 |
| WO | WO 99/04750 | 2/1999 |
| WO | WO 00/12588 | 3/2000 |

OTHER PUBLICATIONS

English Translation of PCT IPER for PCT/EP01/13858, Dated Mar. 11, 2003.
English abstract for DE 19907587, Aug. 24, 2000.
English abstract for DE 19907715, Aug. 24, 2000.
English abstract for EP 1083184, Mar. 14, 2001; and for DE 19951877, May 3, 2001.

* cited by examiner

*Primary Examiner*—Helen L. Pezzuto
(74) *Attorney, Agent, or Firm*—Richard P. Silverman

(57) ABSTRACT

The invention provides water-soluble or water-swellable copolymers obtained by free-radical copolymerization of
A) acryloyldimethyltaurine and/or acryloyldimethyltaurates,
B) optionally, one or more olefinically unsaturated, optionally crosslinking comonomers containing at least one oxygen, nitrogen, sulfur or phosphorus atom and possessing a molecular weight of less than 500 g/mol,
C) one or more at least monofunctional, silicon-containing components capable of free-radical polymerization, the copolymerization
D) taking place in the presence of at least one polymeric additive having number-average molecular weights of from 200 g/mol to $10^9$ g/mol.
The water-soluble or water-swellable copolymers of the present invention are useful in paper processing, laundry detergents, textile processing, petroleum extraction and formulating cosmetics.

6 Claims, No Drawings

SILICONE-MODIFIED COMB POLYMERS BASED ON ACRYLOYLDIMETHYLTAURINE ACID (2-ACRYLAMIDO-2-METHYL-1-PROPANESULFONIC ACID)

The present invention relates to silicon-modified comb polymers based on acryloyldimethyltaurine and/or acryloyldimethyltaurates.

In recent years water-soluble polymers have acquired a continually increasing importance in industry and science. In volume terms, polyelectrolytes are occupying a very large proportion of the overall annual production. They find application, for example, in paper processing, in the laundry detergents industry, in textile processing, in petroleum extraction or as important base materials for cosmetics.

In the cosmetics sector a key role is accorded to polyelectrolytes. Besides water-soluble surface-active substances there is a high demand in this sector for systems which thicken oil and water. Thickeners of this kind, particularly the "super-absorbents" prepared on the basis of polyacrylic acid, have progressed since their development in the 1970s to become a pillar of the hygiene sector. In their crosslinked versions, partly or fully neutralized polyacrylic acids and their water-soluble copolymers are employed in numerous cosmetic formulations as bodying agents. The diversity of possible structures and the diverse possible applications associated therewith are manifested not least in a host of patents filed worldwide since the mid-1970s.

In the 1990s, innovative thickeners based on 2-acrylamido-2-methyl-1-propane-sulfonic acid (AMPS) and their salts were introduced into the market (EP 816 403 and WO 98/00094). In both homopolymer and copolymer form (®Aristoflex AVC, Clariant GmbH) such thickeners are superior in many respects to the corresponding polycarboxylates (Carbopols). For example, thickener systems based on AMPS display outstanding properties in pH ranges below pH 6, i.e., in a pH range in which it is no longer possible to operate with conventional polycarboxylate thickeners. Moreover, the microgel structure of such thickeners leads to a particularly pleasant skin sensation. The ease of processing and the favorable toxicological profile of the principal monomer imbue these thickeners with a high application potential.

Over recent years representatives of a new thickener design have entered the market. In these thickeners, two different properties have been combined in one polymer, thereby opening up new fields of application. Thickening emulsifiers or dispersants are but two examples of this new class of substance. Brand names that may be mentioned include the Pemulens® TR-1 and TR-2 from BF Goodrich or the Aculyn® products from Rohm & Haas. All existing versions are based on hydrophobically modified versions of the conventional polyacrylates.

The aim of this invention was to synthesize a new class of polymer based on the concept of the molecular combination of properties, intended to allow the formulator to stabilize and/or to thicken aqueous systems containing silicone oil. Through free-radical copolymerization of acryloyldimethyltaurine (AMPS) and/or acryloyldimethyltaurates, in the presence where appropriate of further comonomers or polymeric additives, and suitable vinylic mono- or polyfunctional silicone derivatives, it proved possible to synthesize both crosslinked and noncrosslinked structures having advantageous performance properties. A particular possibility with the newly developed structures is the stabilization of silicone-containing emulsions with very high fractions of silicone oil (>30%). Advantageously, emulsions of this kind display a very pleasant skin sensation.

The invention provides water-soluble or water-swellable copolymers obtainable by free-radical copolymerization of A) acryloyldimethyltaurine and/or acryloyldimethyltaurates,
B) if desired, one or more olefinically unsaturated, optionally crosslinking comonomers containing at least one oxygen, nitrogen, sulfur or phosphorus atom and possessing a molecular weight of less than 500 g/mol,
C) one or more at least monofunctional, silicon-containing components capable of free-radical polymerization, the copolymerization
D) taking place in the presence of at least one polymeric additive having number-average molecular weights of from 200 g/mol to $10^9$ g/mol.

The copolymers of the invention preferably possess a molecular weight of from $10^3$ g/mol to $10^9$ g/mol, more preferably from $10^4$ to $10^7$ g/mol, very preferably from $5*10^4$ to $5*10^6$ g/mol.

The acryloyldimethyltaurates can be the organic or inorganic salts of acryloyl-dimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1–C_{22})$-alkyl radicals which if desired may be occupied by up to 3 $(C_2–C_{10})$-hydroxyalkyl groups. Preference is also given to mono- to triethoxylated ammonium compounds with a different degree of ethoxylation. It should be noted that the invention also embraces mixtures of two or more of the abovementioned representatives.

The degree of neutralization of the acryloyldimethyltaurine can be between 0 and 100%, particular preference being given to a degree of neutralization of more than 80%.

Based on the total mass of the copolymers, the amount of acryloyldimethyltaurine and/or acryloyidimethyltaurates is at least 0.1% by weight, preferably from 20 to 99.5% by weight, more preferably from 50 to 98% by weight.

As comonomers B) it is possible to use all olefinically unsaturated monomers whose reaction parameters allow copolymerization with acryloyidimethyltaurine and/or acryloyidimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 22. Particularly preferred unsaturated carboxylic acids are acrylic acid, methacrylic acid, styrenesulfonic acid, maleic acid, fumaric acid, crotonic acid, itaconic acid, and senecic acid. Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another are $(C_1–C_{22})$-alkyl radicals or $(C_2–C_{10})$-hydroxyalkyl radicals. It is additionally possible to employ mono- to triethoxylated ammonium compounds with a different degree of ethoxylation.

The degree of neutralization of the carboxylic acids can be between 0 and 100%, and more preferably is above 80%.

Further preferred comonomers are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl] succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable polymerizable silicone-containing components C) are all compounds which are olefinically at least monounsaturated and capable of free-radical copolymerization under the reaction conditions chosen in each case with acryloyldimethyltaurine and/or acryloyldimethyltaurate and, if desired, further comonomers. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicon-containing components are those of formula (I)

$$R^1-Z-[(Si(R^3R^4)—O—)_w—(Si(R^5R^6)—O)_x—]—R^2 \quad (I)$$

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl (CH$_2$=CH—CO—), methacryloyl (CH$_2$=C[CH$_3$]—CO—), crotonyl, senecionyl, itaconyl, maleyl, fumaryl or styryl radical.

The attachment of the silicone-containing polymer chain to the reactive end group $R^1$ sometimes requires a suitable chemical bridge Z. Preferred bridges Z are —O—, —((C$_1$–C$_{50}$)alkylene)-, —((C$_6$–C$_{30}$)arylene)-, —((C$_5$–C$_8$) cycloalkylene)-, —((C$_1$–C$_{50}$)-alkenylene)-, -(polypropylene oxide)$_n$-, -(polyethylene oxide)$_o$-, -(polypropylene oxide)$_n$ (polyethylene oxide)$_o$-, where n and o independently of one another denote numbers from 0 to 200 and the distribution of the EO/PO units can be random or in the form of blocks. Further suitable bridge groups Z are —((C$_1$–C$_{10}$)alkyl)-(Si(OCH$_3$)$_2$)— and —(Si(OCH$_3$)$_2$)—.

The polymeric central moiety is represented by silicone-containing repeating units. The radicals $R^3$, $R^4$, $R^5$, and $R^6$ denote independently of one another —CH$_3$, —O—CH$_3$, —C$_6$H$_5$ or —O—C$_6$H$_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

$R^2$ can first symbolize an aliphatic, olefinic, cycloaliphatic, arylaliphatic or aromatic (C$_1$–C$_{50}$) hydrocarbon radical (linear or branched) or —OH, —NH$_2$, —N(CH$_3$)$_2$, —$R^7$ or stand for the structural unit [-Z-$R^1$]. The definition of the two variables Z and $R^1$ has already been explained. $R^7$ stands for further Si-containing groups. Preferred $R^7$ radicals are —O—Si(CH$_3$)$_3$, —O—Si(Ph)$_3$, —O—Si(O—Si(CH$_3$)$_3$)$_2$CH$_3$), and —O—Si(O—Si(Ph)$_3$)$_2$Ph).

If $R^2$ is an element of the group [-Z-$R^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following such components with acrylic or methacrylic modification:

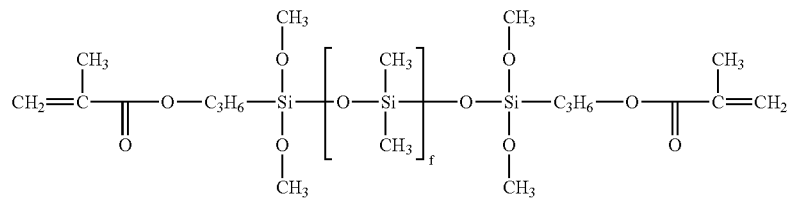

methacryloyloxypropyldimethylsilyl-endblocked polydimethylsiloxanes (f=2 to 500)

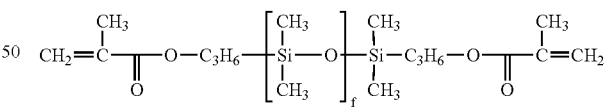

methacryloyloxypropyl-endblocked polydimethylsiloxanes (f=2 to 500)

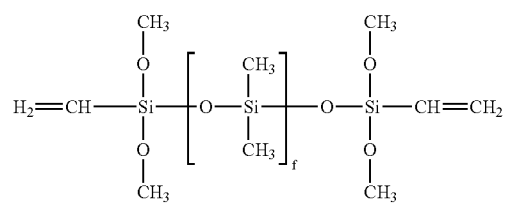

vinyldimethoxysilyl-endblocked polydimethylsiloxanes (f=2–500).

The weight fraction of the comonomers D), based on the total mass of the copolymers, is from 0.1 to 99.9% by weight, preferably from 0.1 to 50% by weight, more preferably from 0.2 to 40% by weight, and very preferably from 0.5 to 30% by weight.

In one preferred embodiment the copolymerization is conducted in the presence of at least one polymeric additive D), the additive D) being added wholly or partly in solution to the polymerization medium before the actual copolymerization. The use of two or more additives D) is likewise in accordance with the invention. Crosslinked additives D) may likewise be used.

The additives D) or mixtures thereof must only be wholly or partly soluble in the chosen polymerization medium.

During the actual polymerization step the additive D) has a number of functions. On the one hand it prevents the formation of overcrosslinked polymer fractions in the copolymer which forms in the actual polymerization step, and on the other hand the additive D) is statistically attacked by active free radicals in accordance with the very well-known mechanism of graft copolymerization. Depending on the particular additive D), this results in greater or lesser fractions of the additive being incorporated into the copolymers. Moreover, suitable additives D) possess the property of altering the solution parameters of the copolymers which form during the free-radical polymerization reaction in such a way that the average molecular weights are shifted to higher values. As compared with analogous copolymers prepared without the addition of the additives D), those prepared with the addition of additives D) advantageously exhibit a significantly higher viscosity in aqueous solution.

Preferred additives D) are homopolymers and copolymers which are soluble in water and/or alcohols. The term "copolymers" also comprehends those having more than two different monomer types.

Particularly preferred additives D) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols. Particularly preferred additives D) are polyvinylpyrrolidones (e.g., K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives D) is preferably from $10^3$ to $10^7$ g/mol, more preferably from $0.5*10^4$ to $10^6$ g/mol.

The amount in which the polymeric additive D) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably di-acrylates and tri-acrylates and/or -methacrylates, more preferably butanediol and ethylene glycol diacrylate and/or methacrylate, trimethylolpropane triacrylate (TMPTA) and trimethylolpropane trimethacrylate (TMPTMA); allyl compounds, preferably allyl(meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

A particularly preferred crosslinker is trimethylolpropane trimethacrylate (TMPTMA).

The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electro-magnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide (DLP) or azo initiators, such as azodiisobutyronitrile (AIBN), for example. Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

The polymerization reaction can be conducted, for example, as a precipitation polymerization, emulsion polymerization, solution polymerization, bulk polymerization or gel polymerization. Particularly advantageous for the profile of properties of the copolymers of the invention is precipitation polymerization, preferably in tert-butanol.

The copolymers of the invention put the user in a position for the first time to thicken silicone oils, possibly in high concentration, in water, or else, in the case of highly modified versions, to thicken silicone oils themselves. Accordingly, formulations with a strong silicone oil character in stick form or gel form, for example, become possible without the deleterious liquid consistency of oils.

It is additionally possible using the polymers of the invention to prepare emulsions with conventional oils which contain Si-containing emulsifiers (possibly also silicone oils), since this combines the properties of silicone oils and conventional oils and also enables the stability of the emulsion by thickening the phases. All of these emulsions exhibit an extremely good gloss, which is of great significance for a cosmetic emulsion. A particular feature is the outstanding skin sensation of these formulations as compared with conventional formulations. In the case of applications in the hair cosmetology segment, the pleasant conditioning effect of the polymers is evident, as are the ease of combing and the shine.

The copolymers of the invention can be employed, inter alia, in W/O emulsions, O/W emulsions, skin protection formulations, shampoos, rinses, treatments, decorative cosmetics such as lipsticks, lipcare sticks or lotions, etc., makeup such as liquid makeup, cover and resist makeup, makeup powder, etc., stick deodorants, antiperspirants, body washes, liquid soap, bar soap, cleansing milk, sun protection formulations, permanent waves, hair colorants, hair gels, and hair sprays, to name but a few. In the case of face makeup, for example, it should be emphasized that by using the polymers of the invention it is possible to absorb excess sebum.

The following examples serve to illustrate the invention without, however, restricting it thereto.

EXAMPLE 1

| Reactants | amount (g) |
|---|---|
| $NH_4$ acryloyldimethyltaurate | 80 |
| Vinyldimethoxyethyl-endblocked dimethicone (® GP-501, Genesee Pol. Corp.) | 20 |
| t-Butanol | 400 |
| Dilauroyl peroxide (initiator) | 1 |
| Poly-N-vinylpyrrolidone (® K-15 BASF) | 5 |

The polymer was prepared by the precipitation method in tert-butanol. The monomers in t-butanol were introduced as an initial charge, the reaction mixture was rendered inert, and then, after initial heating, the reaction was initiated by addition of DLP. The polymer was isolated by removal of the solvent under suction and by subsequent vacuum drying. In 1% strength aqueous solution the polymer exhibits a viscosity of 45 000 mPas with a slightly opalescent appearance. The skin sensation of the gel is markedly superior to that of silicone-free versions.

EXAMPLE 2

| Reactants | amount (g) |
|---|---|
| $NH_4$ acryloyldimethyltaurate | 70 |
| N-Vinylpyrrolidone | 5 |
| Methacryloyloxypropyldimethicone (® GP-446, Genesee Pol. Corp.) | 15 |
| Isopropanol | 500 |
| Azobisisobutyronitrile (initiator) | 1 |

The polymer was prepared by the solution polymerization method in isopropanol. The monomers were dissolved in the corresponding alcohol, the reaction mixture was rendered inert, and then, after initial heating, the reaction was initiated by addition of diazoisobutyronitrile. The polymer solution was subsequently concentrated and the polymer was isolated by vacuum drying.

EXAMPLE 3

| Reactants | amount (g) |
|---|---|
| Acryloyldimethyltaurine (AMPS) | 80 |
| Methacryloyloxypropyldimethicone (® GP-478, Genesee Pol. Corp.) | 20 |
| Cyclohexane | 200 |
| Water | 300 |
| ® Span 80 (sorbitan ester) | 1 |
| $Na_2S_2O_8$ (initiator) | 1 |

The polymer was prepared by the emulsion method in water. The monomers were emulsified in water/cyclohexane using Span ®80, the reaction mixture was rendered inert using $N_2$, and then, after initial heating, the reaction was initiated by addition of sodium peroxodisulfate. The polymer emulsion was subsequently evaporated down (with cyclohexane acting as azeotrope former for water) and the polymer was thereby isolated.

EXAMPLE 4

| Reactants | amount (g) |
|---|---|
| $NH_4$ acryloyldimethyltaurate | 80 |
| Monofunctionalized ethoxylated siloxane (methacrylic, ® Silvet Y-12867, Witco) | 15 |
| t-Butanol | 300 |
| Dilauroyl peroxide | 1 |

The polymer was prepared by the precipitation method in tert-butanol. The monomers in t-butanol were introduced as an initial charge, the reaction mixture was rendered inert, and then, after initial heating, the reaction was initiated by addition of DLP. The polymer was isolated by removal of the solvent under suction and by subsequent vacuum drying.

In 1% strength solution in distilled water the polymer exhibited a clear appearance with a viscosity of 35 000 mPas. In comparison thereto the silicone-free version, with the same composition, exhibited a similar appearance and a viscosity of 12 000 mPas under identical measurement conditions. The skin sensation of the silicone-containing polymer is markedly improved over that of the comparison standards.

EXAMPLE 5

| Reactants | amount (g) |
|---|---|
| Na acryloyldimethyltaurate | 50 |
| Monofunctionalized (methacrylically), ethoxylated siloxane (® Silvet 7608 WITCO) | 45 |
| t-Butanol | 300 |
| Trimethylolpropane triacrylate | 1.8 |
| Azabisamidopropyl hydrochloride | 1 |
| Poly[N-vinylformamide] | 8 |

The polymer was prepared by the precipitation method in tert-butanol. The monomers in t-butanol were introduced as an initial charge, the reaction mixture was rendered inert, and then, after initial heating, the reaction was initiated by addition of ABAH. The polymer was isolated by removal of the solvent under suction and by subsequent vacuum drying.

What is claimed is:

1. A water-soluble or water-swellable copolymer obtained by free-radical copolymerization of
   A) acryloyldimethyltaurine or acryloyldimethyltaurates, or mixtures thereof,
   B) optionally, one or more olefinically unsaturated, comonomer containing at least one oxygen, nitrogen, sulfur or phosphorus atom and possessing a molecular weight of less than 500 g/mol,
   C) one or more at least monofunctional, silicon-containing component capable of free-radical polymerization,
   D) optionally taking place in the presence of at least one polymeric additive having number-average molecular weights of from 200 g/mol to $10^9$ g/mol.

2. The water-soluble or water-swellable copolymer of claim 1, wherein the copolymer is crosslinked.

3. The water-soluble or water-swellable copolymer of claim 1, wherein the copolyrner is copolymerized by precipitation polymerization in tert-butanol.

4. A water-soluble or water-swellable copolymer obtained by free-radical copolymerization of acryloyldimethyltaurine or acryloyldimethyltaurates, and mixtures thereof and one or more at least monofunctional, sllicon-containing component capable of free-radical polymerization, at least one silicon-containing component being a compound selected from the group consisting of at least one silicon-containing component being a compound selected from the group consisting of where f=2 to 500, where f=2 to 500 where f=2 to 500, where f=2 to 500 where f=2 to 500, and mixtures thereof.

5. The water-soluble or water-swellable copolymer of claim 1, wherein component A is present in an amount from 20 to 99.5 weight percent based on said copolymer.

6. The water-soluble or water-swellable copolymer of claim 1, wherein the acryloyldimethyltaurine or acryloyldimethyltaurates, and mixtures thereof is present in an amount from 50 to 99.5 weight percent based on said copolymer.

where f=2 to 500, and mixtures thereof, the copolymerization

* * * * *